United States Patent
Wheatley et al.

(10) Patent No.: US 6,171,335 B1
(45) Date of Patent: Jan. 9, 2001

(54) HEART VALVE PROSTHESIS

(75) Inventors: David John Wheatley, Glasgow; John Fisher, Leeds; David Williams, Frodsham, all of (GB)

(73) Assignee: Aortech Europe Limited (GB)

( * ) Notice: Under 35 U.S.C. 154(b), the term of this patent shall be extended for 0 days.

(21) Appl. No.: 09/355,215
(22) PCT Filed: Jan. 22, 1998
(86) PCT No.: PCT/GB98/00211
  § 371 Date: Nov. 10, 1999
  § 102(e) Date: Nov. 10, 1999
(87) PCT Pub. No.: WO98/32400
  PCT Pub. Date: Jul. 30, 1998

(30) Foreign Application Priority Data

Jan. 24, 1997 (GB) .................................................. 9701479

(51) Int. Cl.$^7$ ...................................................... A61F 2/24
(52) U.S. Cl. .................. 623/2.17; 623/2.33; 623/2.12
(58) Field of Search ............................... 623/2.1 S, 2.18, 623/2.28, 2.3, 2.1, 2.33, 2.21–2.24, 2.12–2.19

(56) References Cited

U.S. PATENT DOCUMENTS

| | | | |
|---|---|---|---|
| 4,364,127 | * 12/1982 | Pierce et al. | 63/2.17 |
| 4,731,074 | * 3/1988 | Rousseau et al. | 623/2.19 |
| 4,888,009 | * 12/1989 | Lederman et al. | 623/2.17 |
| 5,500,016 | * 3/1996 | Fisher | 623/2.17 |
| 5,653,749 | 8/1997 | Love et al. | 623/2 |
| 6,086,612 | * 7/2000 | Jansen | 623/2.17 |

FOREIGN PATENT DOCUMENTS

| | | |
|---|---|---|
| 0 193 987 | 9/1986 | (EP) . |
| 93/18721 | 9/1993 | (WO) . |

\* cited by examiner

*Primary Examiner*—David H. Willse
*Assistant Examiner*—Suzette J. Jackson
(74) *Attorney, Agent, or Firm*—Ratner & Prestia

(57) ABSTRACT

The invention provides a prosthetic valve having a generally annular frame with three post and three scallops. The frame is tri-symmetric with an axis of symmetry defined by the axis of blood flow through the valve. The external surface of the frame is generally cylindrical with diameter D. Each leaflet has a truncated spherical surface adjacent to its free edge. The spherical surface is joined tangentially to a truncated conical surface. The half angle of the truncated cone is approximately 37.5°. The radius of the sphere is approximately D/2−0.5 (mm). The leaflet surface is axisymmetrical with the axis of symmetry being perpendicular to the axis of the valve frame and blood flow.

19 Claims, 8 Drawing Sheets

HEART VALVE PROSTHESIS

This application is the U.S. national phase application of PCT International Application No. PCT/GB98/00211 filed Jan. 22, 1998.

The present invention relates to medical implants, particularly cardiac and vascular implants and prostheses.

In mammals the heart is a vital organ responsible for maintaining an adequate flow of blood (and hence oxygen and nutrients) to all parts of the body. The blood is prevented from flowing backwards through the heart by valves.

Dysfunction of one or more of the valves in the heart can have serious medical consequences. Dysfunction of heart valves may be the result of a congenital defect, or of disease-induced damage or degeneration. Dysfunction results from stenosis or reguritation (or a combination) of the valve, leading to high pressure upstream of the valve.

To date, the only solution to treat some heart valve dysfunctions is to replace the malfunctioning valve. Such a valve replacement operation is expensive and requires specialised facilities for open-heart surgery. Replacement of failed artificial valves carries increased risk and there are practical limits on the number of times that reoperation can be undertaken. This makes the design and operational lifetime of any replacement valve extremely important.

Porcine aortic valves have been used for many years in human patients and it has been proposed (see for example EP-A-0,402,036 of Pro Medica International Inc) to use porcine pulmonary valves in human patients; however, valves derived from biological material have a finite lifetime and must generally be replaced within 10 years of implantation in younger patients.

In third world countries where rheumatic fever is still common, the problems of valve replacement in young patients are considerable. Anticoagulants (required for mechanical valves) are often impractical; accelerated calcification (a problem of biological valves in the young) precludes the use of biological alternatives.

In the Western world, increasing life expectancy for humans results in a corresponding rise in patients requiring cardiac valve replacement. There is thus an increasing need for cardiac valve prostheses having both an extended useful lifetime and also a low risk of inducing thrombosis in a recipient.

Conventional flexible leaflet heart valves are known to comprise an annular frame disposed parallel to the blood flow. The annular frame generally has three posts extending in the downstream direction defining three generally U-shaped openings or scallops between the posts. The leaflets are generally attached to the frame between the posts along the edges of the scallops and are unattached at the free edges of the leaflets adjacent to the downstream ends of the posts.

According to the present invention there is provided a cardiac valve prosthesis comprising a frame and two or more leaflets attached to the frame, wherein at least one of the leaflets comprises a first portion which has a generally spherical surface, and/or a second portion which has a generally conical surface.

The respective surfaces are preferably partially conical or spherical.

The prosthesis may be an artificial valve and may be oriented in a particular direction in a heart (or other vascular tissue) to allow flow of blood in one direction through the tissue but prevent back-flow. The frame preferably has a generally circular cross section with two or more posts (in an equal number to the number of leaflets) extending in the same direction from a base. The prothesis is preferably oriented with the posts of the frame extending in the downstream direction such that the mouth of the valve formed by the base is held open. The leaflets are attached to the frame between the posts and each has a free edge adjacent to the ends of the posts which can seal together to close the valve at the ends of the posts.

The conical portion is preferably located adjacent to the base of the prosthesis, and the spherical portion is preferably located adjacent to the free edge. This is advantageous in that the spherical surfaces at the leaflet edges seal more effectively than planar or conical surfaces, and the conical portion at the base of the valve opens more readily upon the increase of blood pressure in that vicinity than an equivalent spherical portion.

A valve embodying the invention has low opening resistance owing to the conical portion reacting first to the increased pressure on the upstream side of the valve. When closed, the increased pressure on the downstream side of the valve forces the free edges of the leaflets together in a substantially parallel arrangement thereby enhancing the seal between the leaflets and reducing the backflow of blood through the valve.

The spherical portion adjacent to the base of the leaflets also confers advantages in the stress distribution when the valve is closed and the pressure is greater downstream than upstream.

The leaflets may (but need not) be identical.

The leaflets preferably number three and the frame comprises three posts.

The leaflets are preferably flexible.

The leaflets may have a defined boundary between the first (spherical) portion and the second (conical) portion, or alternatively, the boundary between these two portions may be phased, for example by adopting a sphere of gradually increasing radius merging with the conical portion. This is acceptable provided that the free edge of the leaflets (or a portion thereof) has a generally spherical surface.

In one embodiment the leaflets extend beyond the top of the posts of the frame.

The leaflets can comprise any biostable, biocompatible thermoplastic elastomer including but not limited to any polyurethane or silicone elastomer or any copolymer or blend based on these elements.

The fabrication route can be any appropriate method, including not only dip moulding but also injection moulding, transfer moulding and similar procedures.

Preferably the leaflets comprise a biostable polyurethane, such as ELASTEON-CSIRO, CHRONOFLEX or TECO-THANE and are dip moulded thereby integrating the leaflets to the supporting frame and posts.

The leaflets may be approximately 100–200 $\mu$m, but the thickness can vary with the material used. The leaflets can themselves vary in thickness, so as to incorporate thick-walled areas and adjacent thin-walled areas. Ridges and/or smooth progressions from thick to thin walled areas are envisaged.

The leaflet surface is preferably axi-symmetrical, with the axis of symmetry being perpendicular to the axis of the valve frame and the intended direction of blood flow. Where the diameter of the frame is distance D (mm), the radius of the sphere preferably lies between D/2 (mm) and (D/2)–2 (mm).

The conical portion is generally truncated and has a half angle within the range 30° to 45° (eg preferably 37.5°).

The frame can be parallel or slightly tapered on the inside and outside, so as to allow a slightly diverged flow.

The pressure required to open the valve is defined by the equation $Et^3/R$ where E is the elastic modulus, t is the leaflet thickness and R is the radius of curvature.

Reversal of the curvature in the centre of the leaflet(s) may also facilitate an opening of the valve.

The prothesis may have incorporate an escape path for trapped air, eg a bleed hole in the frame and/or in one or more leaflets, optionally near the base of each leaflet leading through the frame to the inflow aspect for de-airing of the sub-leaflet space.

Means for protecting the valve from post ensnarement with an implanting suture is useful. This could take the form of a simple extractable suture linking the tips of the posts, or a more sophisticated umbrella-like flexible polyurethane shield (not shown) which could be collapsed and withdrawn through the mitral prosthesis.

A metal frame may be used and the frame can be dip coated with polymer and with facilities for enhancing metal-polymer adhesion. The metal may be titanium or titanium-alloy although any implantable metallic material may be appropriate such as stainless steel or cobalt-chromium alloys.

Alternatively a polymer material may be used for the frame. Two preferred options are a rigid polyurethane and PEEK, polyetheretherketone. Alternative polymers are Delrin (a polyacetal), polyethylene and polysulphone. Any rigid or semi-rigid thermoplastic polymer such as a polyurethane, PEEK, polyacetal, polyethylene, polysulphone, acrylic or similar materials may be used.

Surface modifications to improve biocompatibility may include any of these useful in relation to medical device technology in general.

Surface modifications may be to control the interactions between the valve material and blood in order to prevent protein adsorption, platelet attachment and activation, activation of the clotting cascade and calcification. It is preferable to coat any surface of the valve, primarily including but not limited to the leaflet material.

The surface modification most likely to result in reduced protein adsorption is that of the attachment of phospholipids to the polymer. The principle is that a phospholipid, such as phosphorylcholine, is attached to the polymer surface, this layer mimicking the surface of cells and being resistant to the adsorption of plasma proteins. Since this adsorption is the first event in blood-polymer interactions that triggers all reactions with the clotting cascade and platelets, the inhibition of the process delays or prevents these other effects. Known technologies can be used to coat any type of synthetic prosthetic heart valve. The polymer used for the construction of the valve may be coated with any biomimetic substance, such as a protein, glycoprotein or phospholipid analogue, for the purpose of minimising plasma protein adsorption onto its surface.

A further possibility involves the attachment of antibodies to a surface in order to control the nature of a protein that is adsorbed. For example, it is known that surfaces covered with a layers of albumin are far less thrombogenic than surfaces covered with fibrinogen. Attempts have been made to coat polymers with these proteins but there are many immunological problems associated with the use of proteins derived from sources other than the host. The better concept is to employ anti-albumin antibodies which can be attached to the surface such that when the material comes into contact with the patient's blood, their own albumin becomes strongly attached to the bound antibody.

Platelets have a tendency to interact with all foreign surfaces but this process can be minimised by control of the surface composition and characteristics. It is important to prevent platelets from attaching to the surface but also to prevent any attached platelets from being activated at or near that surface. A surface modification process that could be beneficial involves the attachment of hydrophilic molecules onto the polymer surface. Polyethylene glycol or other similar substances may be covalently attached to polymers such as polyurethane and the imparted hydrophilicity will reduce the tendency for cellular attachment.

Platelet attachment may also be resisted by the use of pharmacologically active agents attached to the surface. Drugs such as prostaglandin, heparin, hirudin, t-plasminogen activator and urokinase have been attached to functionalised polymer surfaces or otherwise incorporated as leachable or diffusable components of polymers for this purpose. These molecules are known to have anti-platelet activity through their effect on platelet membranes and/or their effect on components of the clotting cascade which interact with these membranes and it is possible to reduce platelet attachment and activation.

One or more parts of the prosthesis can be transparent. Particularly preferred materials for use in fabrication of prosthetic valves according to the present invention are based on those disclosed in U.S. Pat. Nos. 5,393,858 and 5,403,912, International Patent Application No. PCT/AU97/00619 and Australian provisional Patent Application Nos. P07002, P07616 and P07878.

An embodiment of the invention will now be described by way of example with reference to the accompanying drawings in which:

FIGS. 1a and b show a valve in perspective view;

Figure 1A:
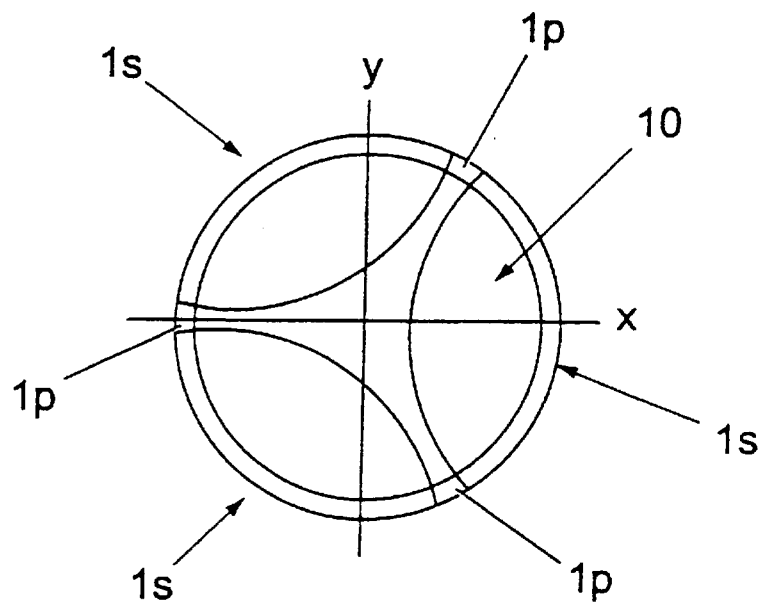
Figure 1B:
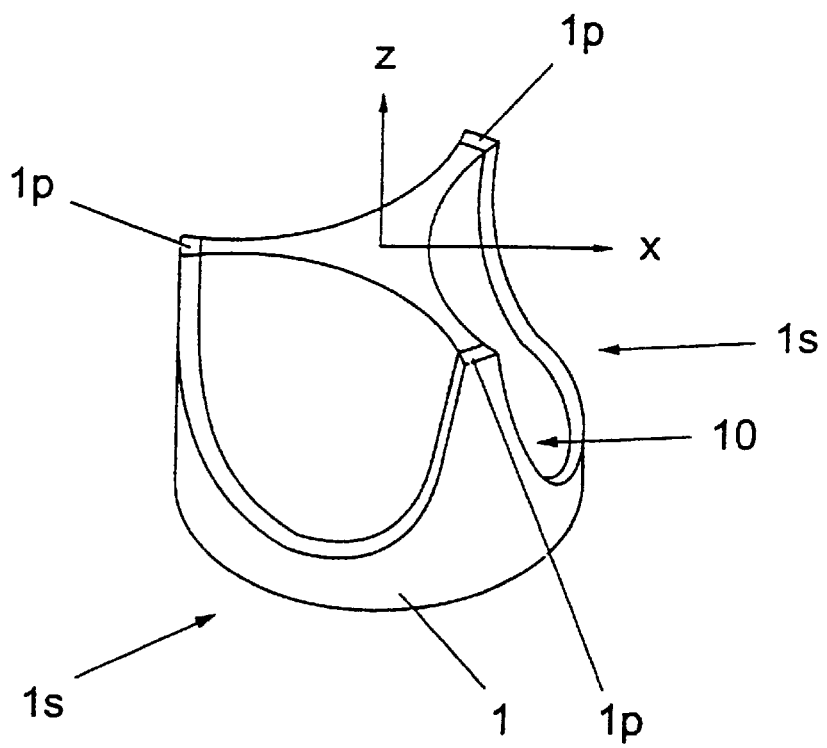

Referring now to the drawings, a prosthesis according to the invention has a generally annular frame 1 with three posts 1P and three scallops 1S. The valve frame 1 is preferably formed from a rigid polymer such as polyetheretheketone or high modulus polyurethane, and is tri-symmetric with an axis of symmetry defined by the axis of blood flow through the valve. The external surface of the frame 1 is generally cylindrical with diameter D, and diverging to the tips of the posts P. For a given diameter D, the thickness of the valve frame 1 is typically 0.05 D.

The three scallops 1S and posts 1P are equally spaced at 120° intervals around the frame. A leaflet 10 is attached along the free edge of each scallop 1S and is supported by adjacent posts 1P. The three leaflets 10 are thus also spaced at 120° intervals around the frame 1.

Figure 3A:
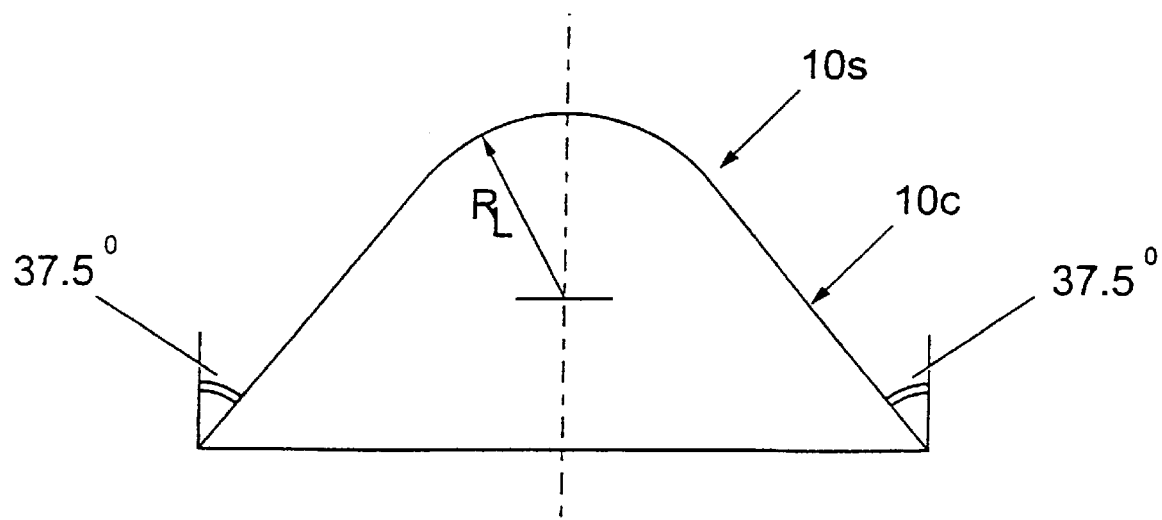
FIG. 3 shows a sectional view through a leaflet of the FIG. 1 and FIG. 2 valves.

Each leaflet 10 is identical, and has a truncated spherical surface 10S adjacent to its free edge. The spherical surface 10S is joined tangentially to a truncated conical surface 10C. The half angle of the truncated cone is 37.5°, but can be any angle in the range from 30° to 45° as shown in FIG. 3. The radius of the sphere is approximately D/2−0.5 (mm), but can be between D/2 and D/2−2 (mm). The leaflet surface is axi-symmetrical with the axis of symmetry being perpendicular to the axis of the valve frame and blood flow.

Figure 3B:
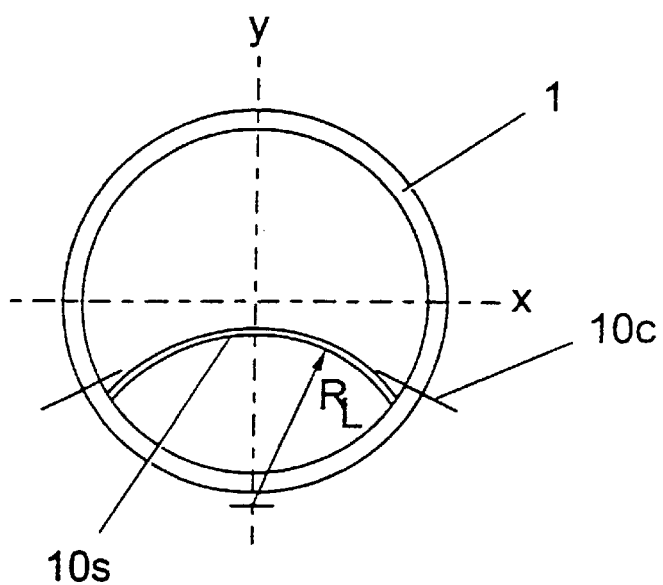
Figure 4A:
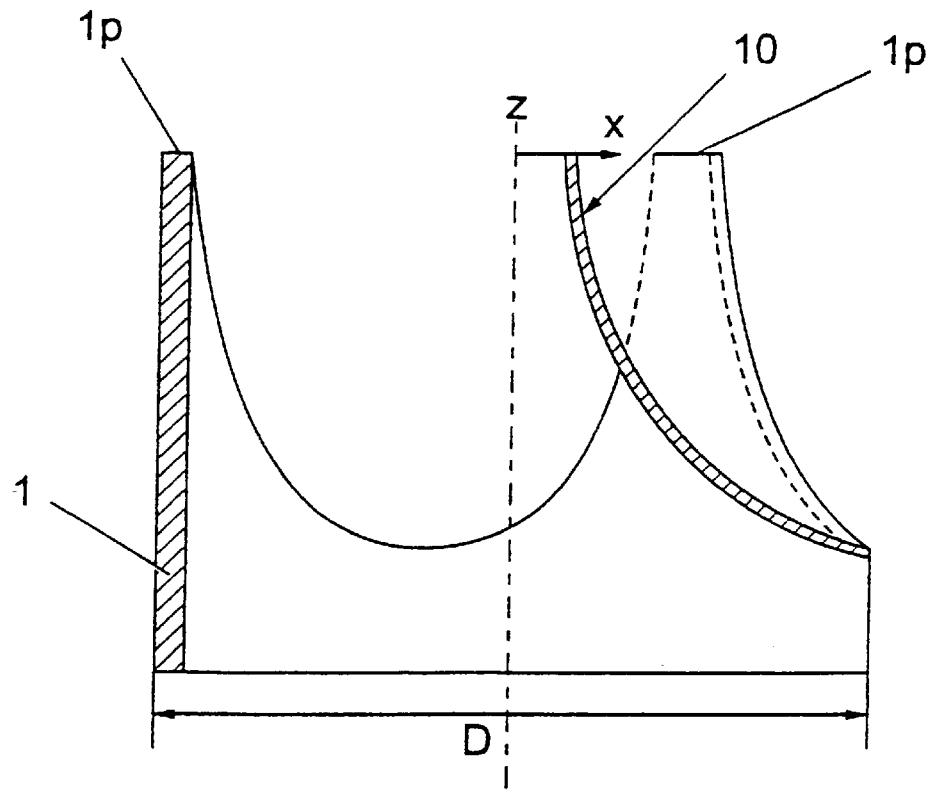
FIG. 4 shows a side sectional view of the FIG. 1 value.
Figure 4B:
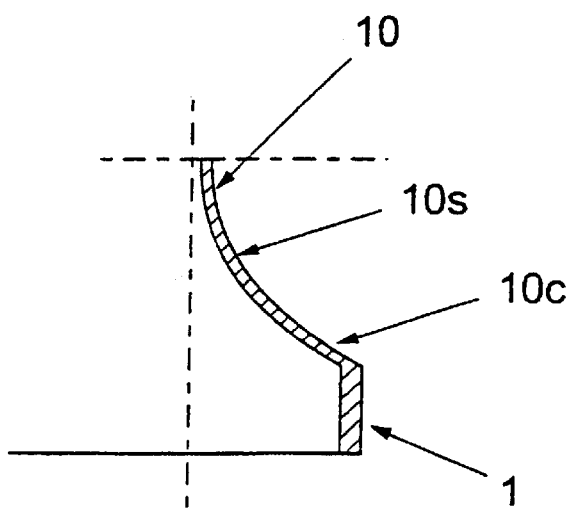
Figure 5:
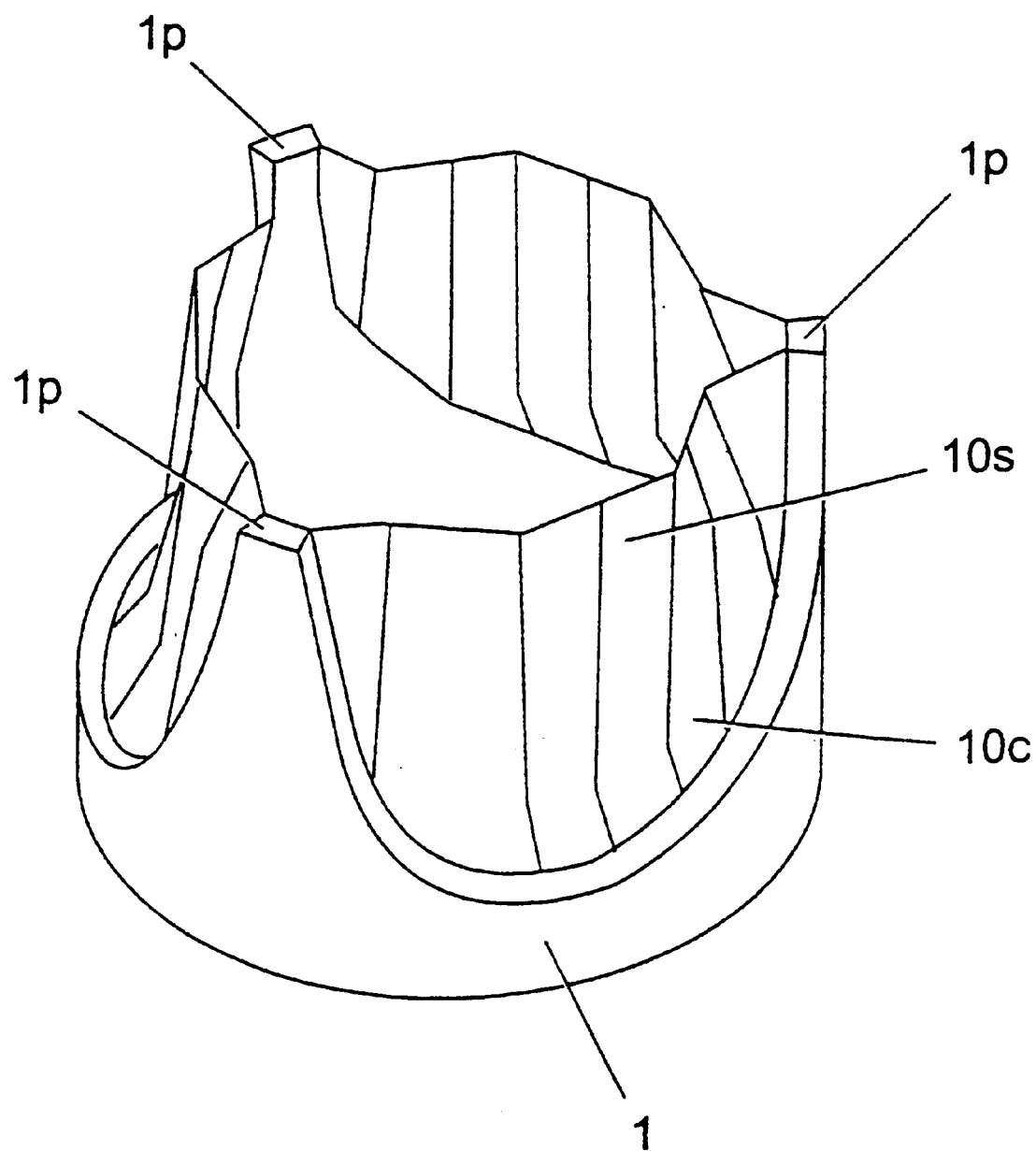
FIG. 5 shows a perspective view of the valve when open.
Figure 6A:
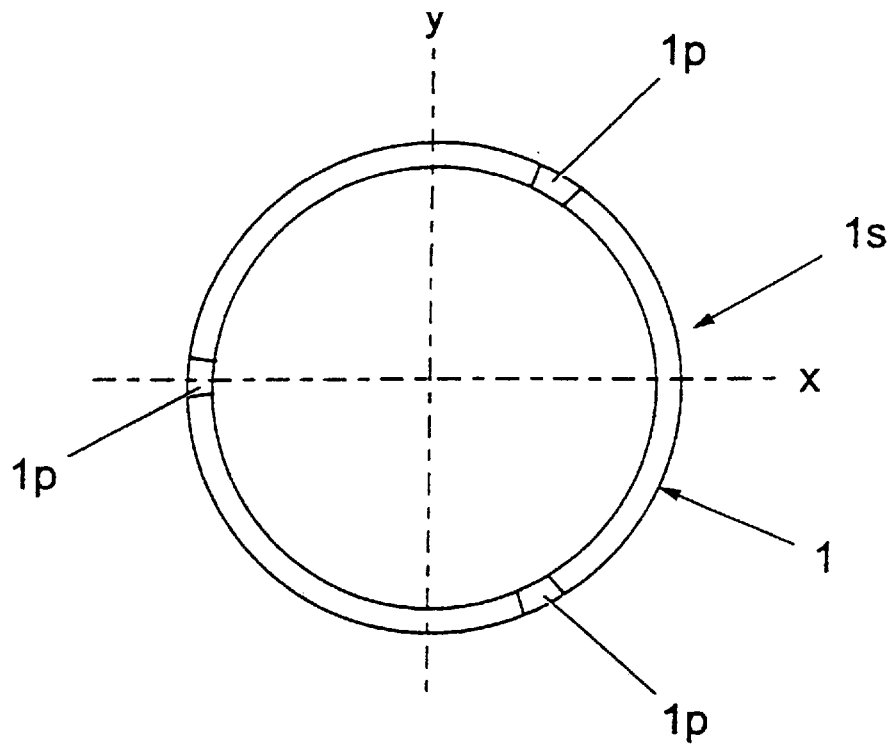
FIG. 6 shows a plan and a perspective view of the frame.
Figure 6B:
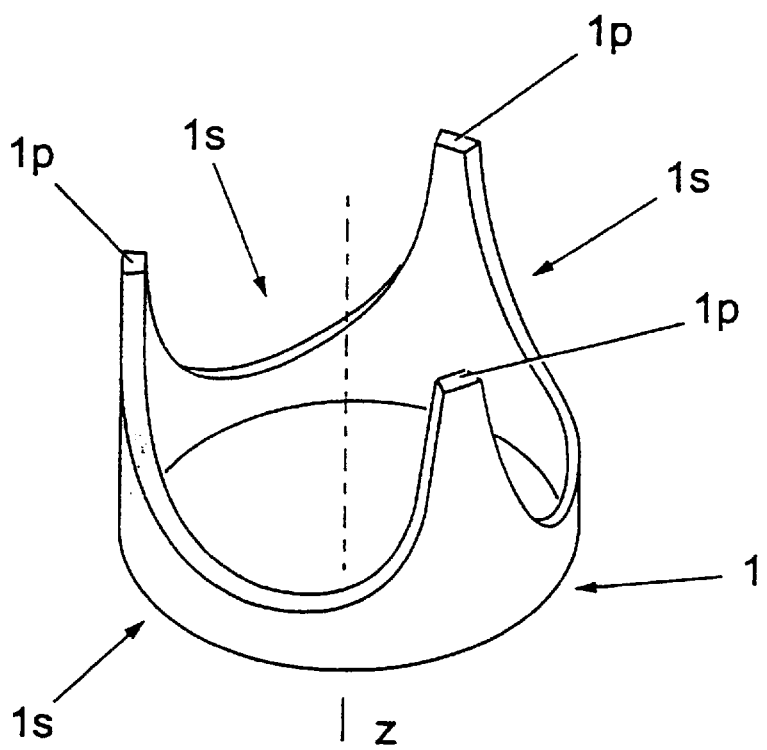
Figure 7:
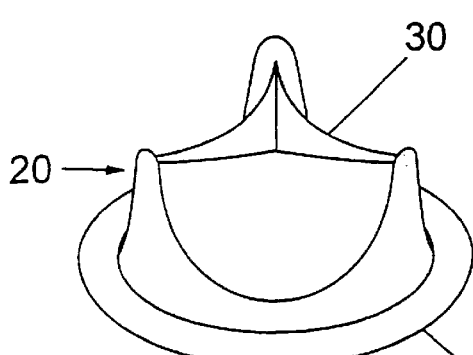
FIG. 7 shows a perspective view of a second valve.
Figure 8:
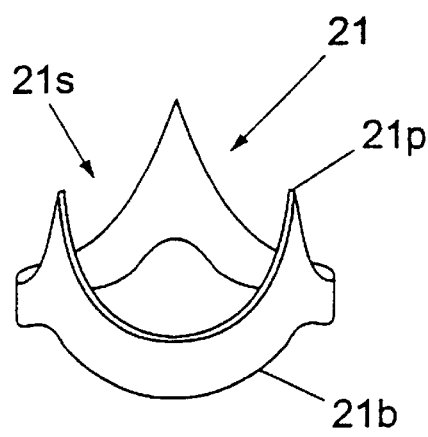
FIG. 8 shows a perspective view of the frame of the FIG. 7 valve.
Figure 9:
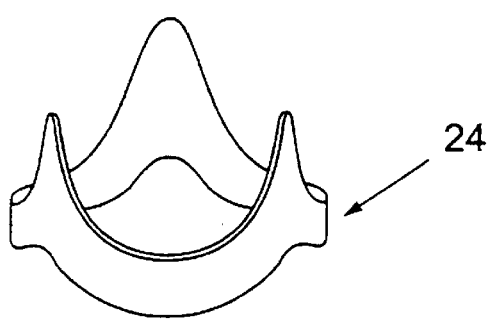
FIG. 9 shows a sleeve of the FIG. 7 valve in perspective view.
Figure 10:
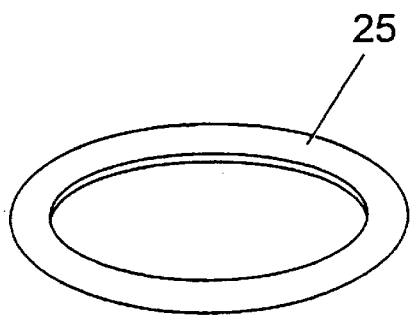
FIG. 10 is a perspective view of a sewing ring of the FIG. 7 valve.
Figure 11:
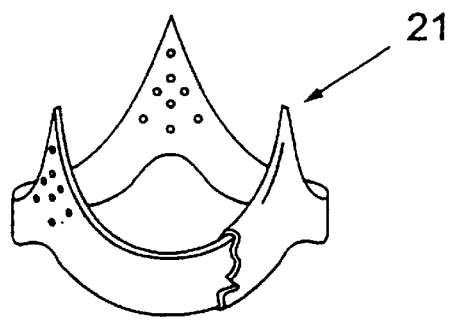
FIG. 11 shows a perspective view of the FIG. 8 frame partially cut-away.
Figure 12:
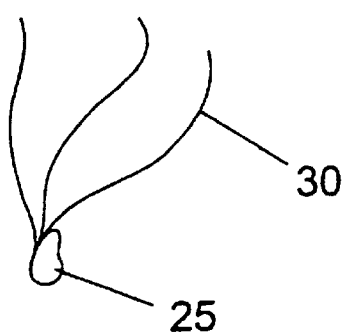
FIG. 12 shows a side sectional view of the leaflets of the FIG. 7 valve.
Figure 13:
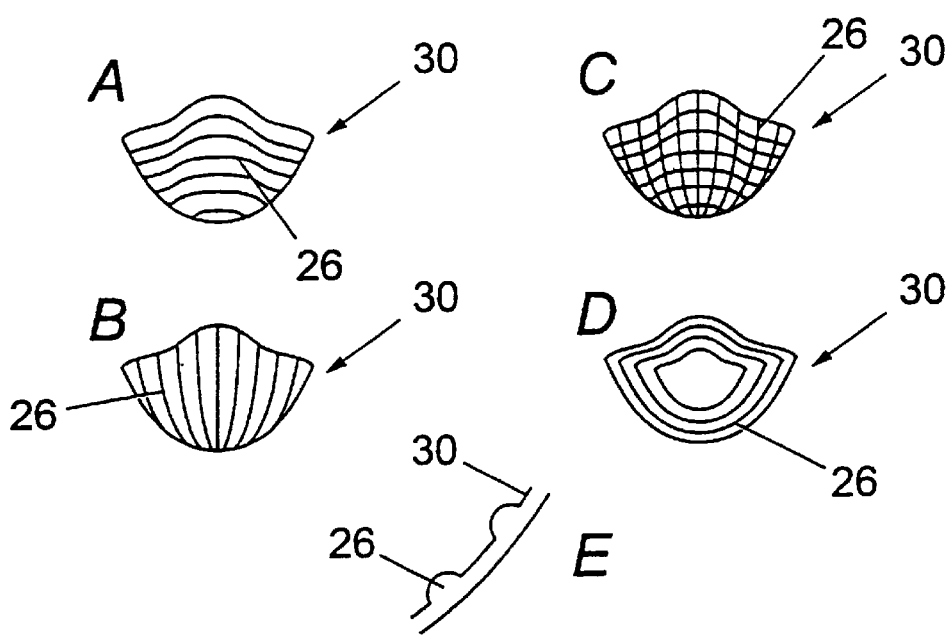
FIG. 13 shows plan views (a, b, c and d) and a cross section (e) of the leaflets indicating possible ribbing configurations.
Figure 14:
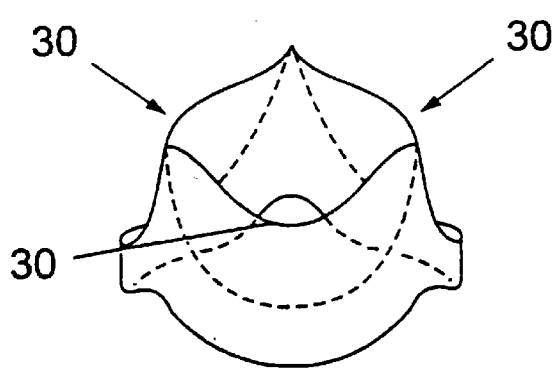
FIG. 14 shows a perspective view of integrally moulded leaflets of the FIG. 7 valve.

The free edge of each leaflet lies in a plane XY perpendicular to the axis of intended blood flow through the valve (Z). FIG. 3b shows the leaflet geometry in the XY plane, and FIG. 4 shows the leaflet geometry in the XZ plane.

The valve is disposed eg in vascular tissue with the post 31 and free edges of the leaflets pointing downstream. The leaflet geometry is designed to encourage the opening of the valve leaflet from the base of the valve. An increase in pressure upstream of the valve causes the conical portions 10C at the base of the leaflets to diverge first. The conical surface can buckle to an open position very easily with minimal resistance, and thus the valve can open under very low upstream pressures. The divergence of the conical sections 10C initiates divergence of the spherical portions 10S.

The spherical portions 10S of the leaflets 10 are easily opened following the divergence under upstream pressure of the conical portions 10C, and under increased downstream pressure, seal against one another more effectively than a conical or a flat surface.

The sealing of the leaflets and competence of the valves may be further enhanced by extending the leaflets 1 to 2 mm above the top of the valve posts, varying the leaflet geometry above the post slightly to bring the leaflets into direct opposition.

FIGS. 7–13 show a second embodiment of a valve according to the invention. The second valve 20 has three leaflets 30 of flexible polyurethane located on a support frame 21, a protective shield 24 for the leaflets 30, and a sewing ring 25 for surgical insertion.

The frame 21 has 3 posts 21P, each tapering to a point from a base 21B. The posts and the base define 3 scallops 21S. The lower (upstream) edge of the base 21B is scalloped to conform generally to the scallops 21S receiving the leaflets 30.

A metal frame 21 is preferred and can provide maximum strength and minimum frame thickness; the frame 21 could be dip coated with polymer. Apertures, grids or a mesh surface could enhance metal/polymer adhesion.

The primary function of the frame 21 is to support the base of the leaflets 30, giving a stable and predictable geometry to the base of the leaflets 30. The origin of the leaflets from the frame should be at an optimised angle to minimise flexion stresses during leaflet motion, and to spread the zone of transition from full flexibility to full rigidity as widely as possible. A seamless attachment of leaflet 30 to frame 21 is desirable to minimise the possibility of separation of leaflet 30 from frame 21.

A degree of flexibility of the frame 21 will be desirable to reduce stress on the leaflets, but resistance to creep is important.

An outer sleeve 24 is provided to surround the posts and frame, and to provide protection to the leaflets 30 from contact with adjacent tissues, particularly ventricular myocardium in the case of the mitral valve, and aortic wall in the case of the aortic valve. The sleeve extends to beyond the edges of the posts.

The frame 21 also provides a secure anchorage for a sewing ring 25 to allow surgical insertion. Additionally, the frame can provide a temporary support for a mounting system to allow surgical handling during implantation of the valve.

Ideally, the frame 21 should be attached to the sewing ring 25 in a manner which allows the implanted valve 20 to be rotated by the surgeon to optimise the position of the frame posts.

Ideally, to minimise the risk of injury to the leaflets 30 during surgical implantation, and to facilitate accurate and secure placement of the sewing ring 25, the frame 21 should be separable from the sewing ring 25, and be readily and securely attachable at the time of surgery following completion of sewing ring 25 insertion.

Overall height of the valve should be as low as is compatible with good leaflet stability and reasonable stress. The base of the leaflets 30 should be located as close to the inflow aspect of the valve as possible, and the sewing ring 25 should be mounted a distance from the inflow aspect to reduce post protrusion as much as possible.

The geometry of the leaflets 30 is preferably optimised for even spread of stress during opening and closing, and there should be substantial zones of leaflet 30 apposition. The leaflets 30 should preferably open at low transvalvar pressure levels to allow satisfactory use in small sizes in the mitral position, as well as to gain optimal haemodynamic function. Hydrodynamic performance in terms of pressure drop should rival that of bileaflet mechanical valves rather than bioprosthetic valves, and that of bioprosthetic valves in terms of regurgitant flow.

Flexible three leaflet valves have essentially two stable positions for the leaflets—open and closed. The transition between the open and closed positions involves a process of rapid buckling, which inflicts rapid changes in shape on the leaflet accompanied by abrupt angulation of the leaflet material and areas of high stress concentration. It is possible to minimise this source of transient, repetitive high stress by careful leaflet geometric design.

The leaflet 30 can be formed with "memory" for the optimised mid-buckling position allowing minimal internal stress at the most vulnerable part of its movement cycle. The leaflets 30 can be dip moulded in a "mid-buckling" position. This offers a solution to the problem of dip moulding three leaflets 30 within a complete frame 21. However, it also helps to ensure that the buckling process is predictable and controlled, with minimisation and distribution of stress during buckling. To ensure that the valve assumes a closed position when unloaded a second dip could be applied while the valve was in the closed position. The same effect may be achievable by heat annealing in the closed position. Whichever method is used, only sufficient memory should be induced in the leaflet to allow closure, but not so much as to require the level of opening transvalve pressure gradient that would be present if the leaflet were moulded in the closed position. It may also be helpful to carry out a third dip mould in the open position (or further heat annealing) to impose a uniform, uncrimped geometry on the open valve. The thickness of additional dip coats would be controlled by adjusting the concentration of the dipping solution.

A further option for both strengthening the leaflets 30 and controlling buckling is provided by incorporating reinforcing ribs 26 in the polyurethane leaflets 30. This has the effect of making the leaflet 30 stiffer in one direction (the direction of the ribs 26) than in the perpendicular direction. The anisotropic properties of the native aortic valve (and porcine bioprosthetic valves) could be mimicked through circumferential ribbing on a polyurethane leaflet. The concept can be extended to the use of grid-like ribs 26 or even concentrically placed circular or oval ribs 26 which would influence leaflet buckling in a predictable fashion. Such ribs 26 can be formed in a dip moulded valve, for example, by carefully etching the leaflet 30 dipping formers. In order to avoid potential flow disturbance, it would be desirable to form the ribs 26 on the leaflet outflow rather than on the inflow surface.

The leaflet 30 may be dip-moulded separately, to facilitate an adequate surface area for the leaflets 30, as well as the ribbing pattern of polyurethane as an inherent part of the leaflet 30 (protruding from the outflow aspect of the leaflets), and may be assembled onto a frame 21 using locating pins and holes.25 Alternatively, it is possible to dip mould all three leaflets as a complete unit which could be bonded or fixed onto a frame eg with the aid of locating pins and corresponding holes in the frame. The sleeve 24 can include a clamp and could extend beyond the posts to assist in shielding the leaflets from myocardial or aortic wall impingement.

EXAMPLE 1

Figure 2:
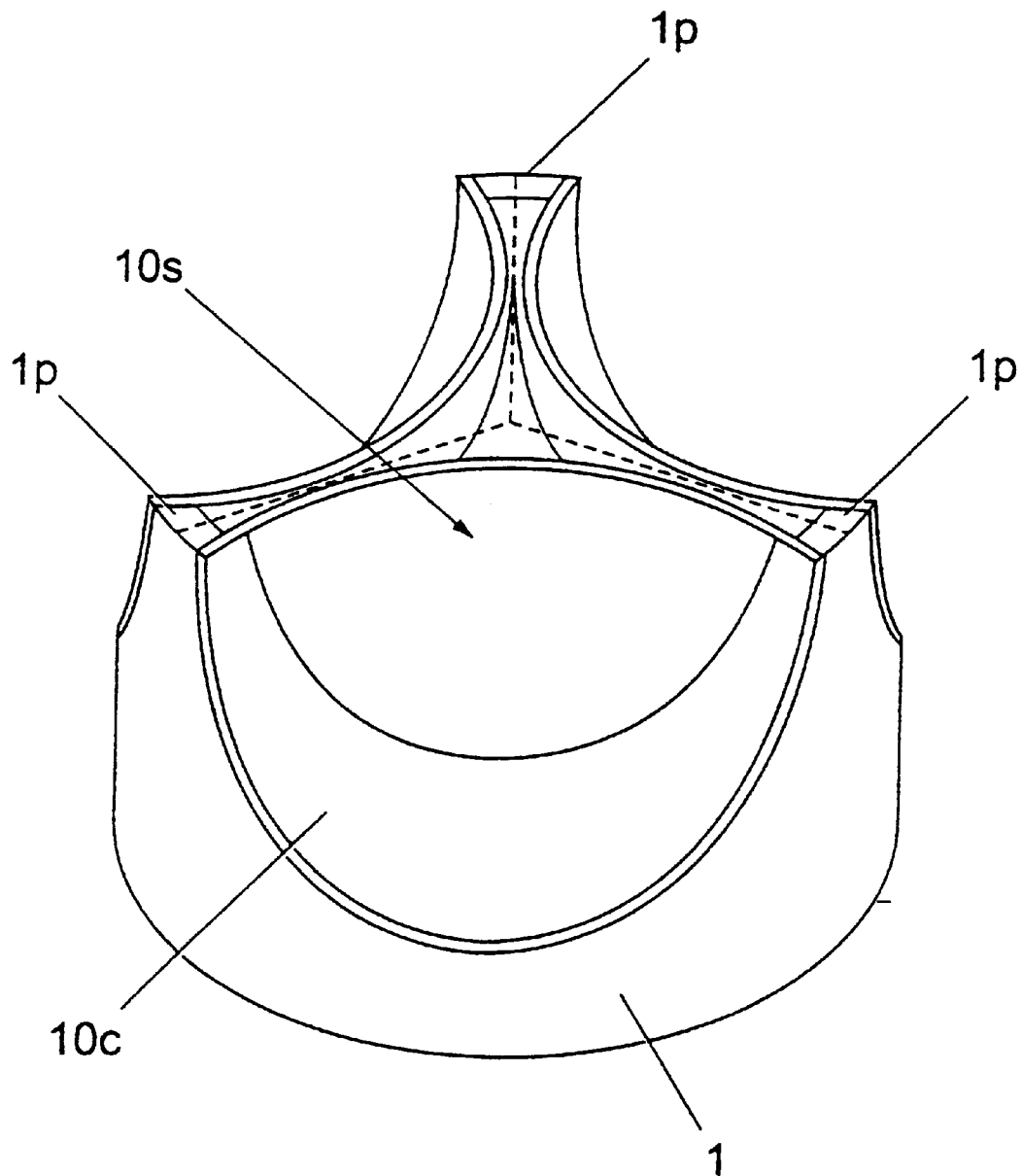
FIG. 2 shows a perspective view of a FIG. 1 valve showing the spherical and conical portions.

A valve was manufactured as shown in FIG. 2. The base has an approximate outer diamter of 23.8 mm with an inner diameter of 22.4 mm.

The posts extend approximately 17 mm from the base of the frame and in this embodiment the width of the top of each post is 1.4 mm with a thickness of 0.7 mm.

The valve frame is manufactured from polyetheretherketone and coated with ELASTEON CSIRO at a thickness of 0.2 mm.

To fabricate the coated valve frame is placed over a solid mound and leaflets are formed by dip moulding thereby integrating them to the frame. The leaflet material is ELASTEON CSIRO polyurethane with a thickness of between 100 to 200 $\mu$m.

Alternative examples of a prosthetic valve according to the present invention involve using a high modulus polyurethane frame (E>500 MPa) or using CHRONOFLEX or TECOTHANE polyurethanes with an elastic modulus in the range 5–15 MPa.

Modifications and improvements can be incorporated without departing from the scope of the invention. For instance, the frame can be made of a biocompatible polymer, metal, or composite. The frame can be coated with polyurethane to allow integration of the leaflets, and can be flexible so as to allow the post to deflect (eg by approximately 0.05 D) on closure of the valve under pressure.

What is claimed is:

1. A cardiac valve prosthesis comprising a frame and two or more leaflets attached to the frame, wherein at least one of the leaflets comprises a first portion which has a generally spherical surface, and a second portion which has a generally conical surface.

2. A prosthesis as claimed in claim 1 wherein the surfaces of the first and second portions are respectively partially spherical or conical.

3. A prosthesis as claimed in any of claim 1 or claim 2 wherein the frame has a generally circular cross section with two or more posts (in an equal number to the number of leaflets) extending in the same direction from a base such that the mouth of the valve formed by the base is held open.

4. A prosthesis as claimed in any of claim 1 or claim 2 wherein the leaflets are attached to the frame between the posts and each have a free edge adjacent to the ends of the posts which can seal together at the ends of the posts.

5. A prosthesis as claimed in any of claim 1 or claim 2 wherein the conical portion is located adjacent to the base of the prosthesis, and the spherical portion is located adjacent to the free edge.

6. A prosthesis as claimed in any of claim 1 or claim 2 wherein the leaflets are identical.

7. A prosthesis as claimed in any of claim 1 or claim 2 wherein the prosthesis comprises three leaflets and three posts.

8. A prosthesis as claimed in any of claim 1 or claim 2 wherein the leaflets are flexible.

9. A prosthesis as claimed in any of claim 1 or claim 2 wherein the leaflets have a defined boundary between the first (spherical) portion and the second (conical) portion.

10. A prosthesis as claimed in any of claim 1 or claim 2 wherein the boundary between the first and second portions is phased by adopting a sphere of gradually increasing radius merging with the conical portion and the free edge of the leaflets (or a portion thereof) has a generally spherical surface.

11. A prosthesis as claimed in any of claim 1 or claim 2 wherein the leaflets comprise a biostable material, such as biostable polyurethane CSIRO, and are dip molded thereby integrating the leaflets to the supporting frame and posts.

12. A prosthesis as claimed in any of claim 1 or claim 2 wherein the leaflets are approximately 100–200 $\mu$m.

13. A prosthesis as claimed in any of claim 1 or claim 2 wherein the leaflets vary in thickness, so as to incorporate thick-walled areas and adjacent thin-walled areas.

14. A prosthesis as claimed in any of claim 1 or claim 2 wherein the leaflet surface is axi-symmetrical, with the axis of symmetry being perpendicular to the axis of the valve frame and the intended direction of blood flow.

15. A prosthesis as claimed in any of claim 1 or claim 2 wherein the diameter of the frame is distance D and the radius of the sphere lies between D/2 and D/2-2 (mm).

16. A prosthesis as claimed in any of claim 1 or claim 2 wherein the conical portion is truncated and has a half angle within the range 30° to 45°.

17. A prosthesis as claimed in any of claim 1 or claim 2 wherein the pressure required to open the valve is defined by the equation $Et^3/R$ where E is the elastic modulus, t is the leaflet thickness and R is the radius of curvature.

18. A prosthesis as claimed in any of claim 1 or claim 2 wherein the prosthesis incorporates an escape path for trapped air.

19. A prosthesis as claimed in any of claim 1 or claim 2 wherein the prosthesis further comprises means for protecting the prosthesis from post ensnarement with an implanting suture.

* * * * *